United States Patent [19]

Uchikawa et al.

[11] Patent Number: 5,212,657

[45] Date of Patent: May 18, 1993

[54] KINETOFRICTIONAL FORCE TESTING APPARATUS

[75] Inventors: Hiroshi Uchikawa; Mutsuo Munekata; Hiroyuki Motohashi, all of Tokyo, Japan

[73] Assignees: Onoda Cement Co., Ltd.; Koyo Precision Instruments, Inc., both of Tokyo, Japan

[21] Appl. No.: 465,499

[22] Filed: Jan. 16, 1990

[30] Foreign Application Priority Data

Feb. 1, 1989 [JP] Japan .................. 1-20907

[51] Int. Cl.⁵ .............................. G01N 19/02
[52] U.S. Cl. .................. 364/556; 364/551.01; 73/9
[58] Field of Search .............. 364/556, 550, 551.01; 73/9

[56] References Cited

U.S. PATENT DOCUMENTS 4,839,754  6/1989  Gami et al. .......... 360/73.01

FOREIGN PATENT DOCUMENTS

| 53-76238 | 1/1980 | Japan | 73/9 |
| 60263653 | 6/1987 | Japan | 73/9 |
| 61196563 | 5/1988 | Japan | 73/9 |
| 63196808 | 2/1990 | Japan | 73/9 |
| 63197398 | 2/1990 | Japan | 73/9 |

Primary Examiner—Vincent N. Trans
Attorney, Agent, or Firm—Leydig, Voit & Mayer

[57] ABSTRACT

A kinetofrictional force testing apparatus has a spindle rotated by a variable speed motor. A load cell is disposed in opposition to a disk coupled to the spindle and includes a test head for the disk, a rotational frequency controlling synthesizer, and a personal computer for general control. The rotational speed of the motor is varied on the basis of clock pulses from the rotational frequency controlling synthesizer associated with the personal computer. The rotational frequency and rotational acceleration/deceleration of the disk coupled to the spindle are digitally controlled by a predetermined program set in the personal computer. The test head is supported by a leaf spring having strain gauges mounted on its lateral surfaces. Frictional forces are measured by the output of the strain gauges.

10 Claims, 5 Drawing Sheets

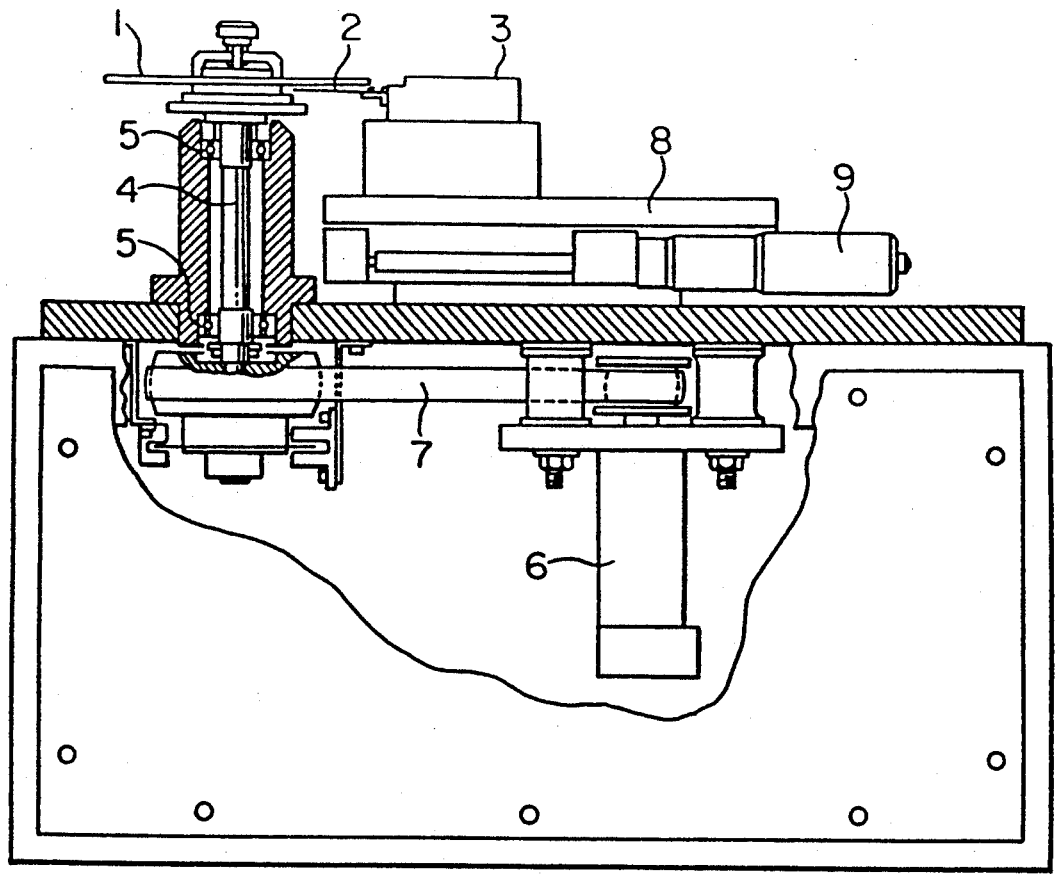
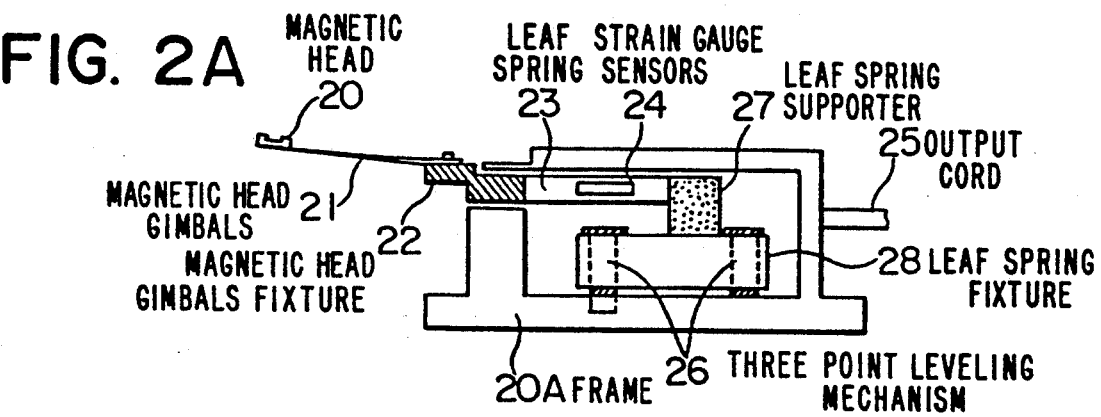
FIG. 2A
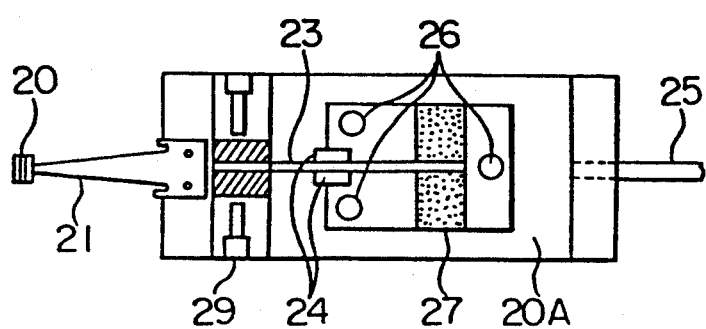
FIG. 2B

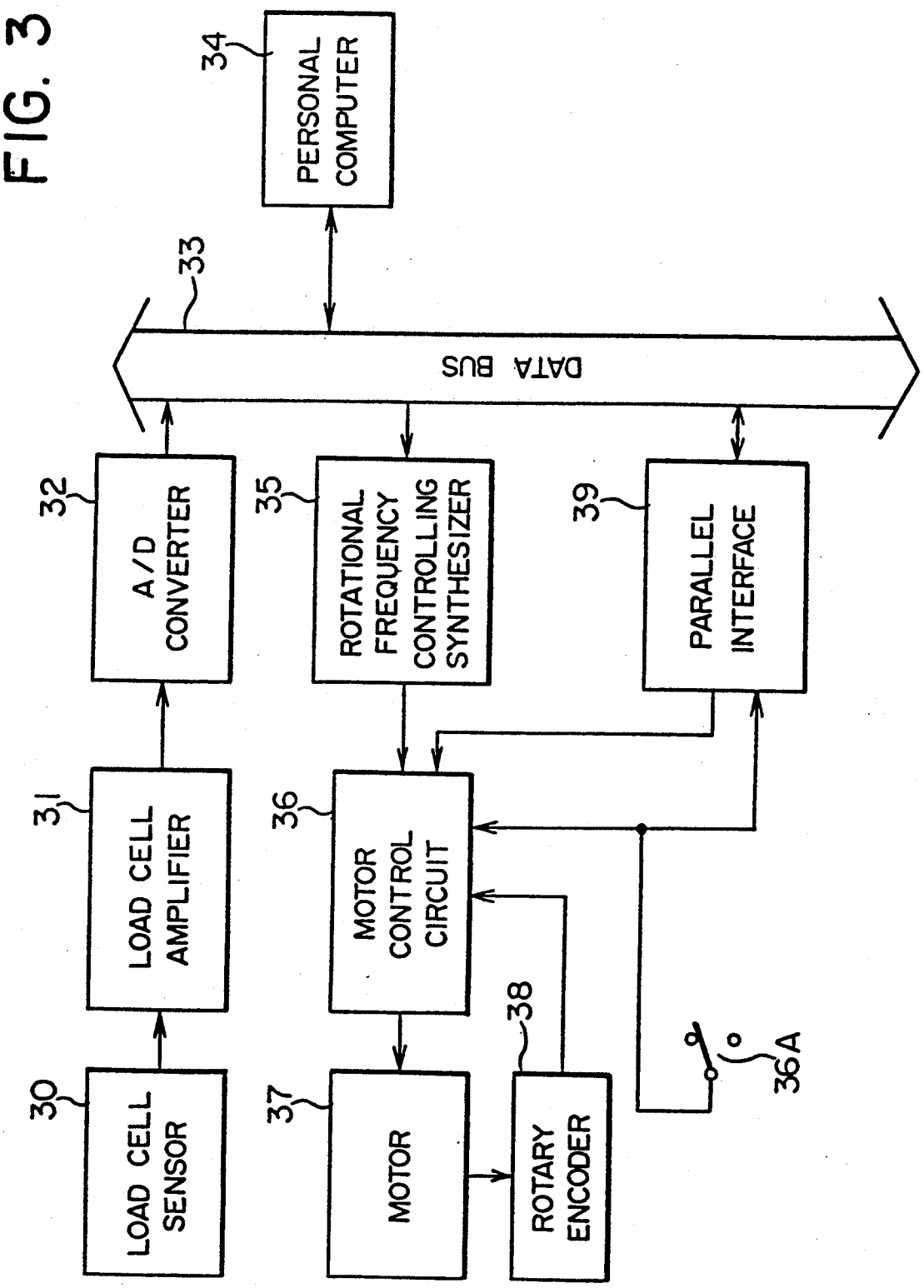

KINETOFRICTIONAL FORCE TESTING APPARATUS

BACKGROUND OF THE INVENTION

This invention relates to a kinetofrictional force testing apparatus. More particularly, it relates to a kinetofrictional force testing apparatus in which a magnetic disk, for example, is used as a sliding member and relative frictional forces generated between the magnetic disk and a corresponding test head, such as a magnetic head by starting and stopping the rotation of the magnetic disk can be measured with a high sensitivity.

Many magnetic disk devices employed in recent years are operated by the so-called contact start/stop method (CSS method). According to this method, while a magnetic disk is a standstill, it is in contact with a magnetic head. After the magnetic disk has started rotating, the magnetic head gradually rises above the surface of the magnetic disk, and when the magnetic disk has reached a certain predetermined rotating speed (usually 3600 RPM), the magnetic head floats above the surface of the magnetic disk.

Assessments of the durability of the magnetic disk and the magnetic head are made by measuring the relative frictional forces between the magnetic disk and the magnetic head, and a test method therefor is clearly prescribed in ANSI Standards. However, these standards contain no stipulations concerning the frequency response of a load cell sensor. Therefore, various test results can be produced depending upon the frequency responses of the load cell sensors used. The frequency responses of the load cell sensors presently in use are at most 50 Hz, and when the rotational frequency of the magnetic disk is raised, the frequency component of the frictional force shifted to a high frequency side and the resonant frequency component of a measuring system are superposed to render accurate measurement impossible. In the prior art technique of this type, accordingly, the rotational frequency must be set at 10 RPM or below for the purpose of enhancing the accuracy of the measurement.

The durability of a magnetic disk device is governed by kinetic frictional characteristics based on the rise and fall of the rotational speed at the start and stop of the magnetic disk device. It is therefore necessary to precisely measure the kinetic frictional forces in the cases where the rotational frequency changes by several hundred RPM in a short time (usually within 1 second).

A rotational drive system for a conventional magnetic disk device is furnished with individual motors for low speeds and for high speeds, and rotational speeds of, for example, 0.1 RPM through 4000 RPM are covered by properly switching and actuating these motors. With such a rotational drive system, however, a complicated mechanism is necessitated, and a wide range of rotational frequencies cannot be continuously controlled in a short time. In addition, a construction is adopted wherein the load cell sensor used is stopped by stopper means, and the load cell sensor is sensitive in a limited direction. It is therefore impossible to use the sensor to measure both the up and down motions of the magnetic head.

SUMMARY OF THE INVENTION

First, in order to continuously measure kinetic frictional forces during the rise and fall of the rotational speed of a magnetic disk, an extensive region from low speed rotations to high speed rotations needs to be covered by a single motor. In addition, the rising and falling characteristics of the rotational speed of magnetic disk devices commercially available are usually different for each product, so when performing kinetofrictional force tests it is indispensable to precisely set the desired rotational speed curves. Further, in order to precisely measure the kinetofrictional forces during abrupt rises and falls in the rotational speed of the magnetic disk device, the resonant frequency of a load cell sensor section including a magnetic head must be heightened by minimizing frequency components which are ascribable to the vibrations of the magnetic disk device itself, the vertical and horizontal movements of the magnetic disk, the vertical vibrations of the magnetic head, etc. Besides, for the purpose of permitting a load cell sensor to be applied to both the up and down motions of the magnetic head, the sensor must be capable of measuring kinetofrictional forces in both the clockwise and counterclockwise directions.

A kinetofrictional force testing apparatus according to this invention comprises a variable-speed motor and a spindle which is rotated by the motor. A load cell is disposed in opposition to a disk coupled to the spindle. The load cell includes a test head for the disk. The test head is supported by a leaf spring having first and second surfaces with force sensing elements attached thereto. According to the invention the motor is controlled by a rotational frequency controlling synthesizer and a personal computer operated by a predetermined program which varies the speed of the motor to carry out a test procedure for kinetofrictional forces as, for example, by setting the same rotational rise and fall characteristic curve as that of a commercially available magnetic disk drive.

The motor which is used in the kinetofrictional force testing apparatus of this invention is a D.C. brushless servomotor which is capable of stable continuous rotations in an extensive region of 0.1–4000 RPM. Unlike the prior art apparatus of this type, therefore, it is not necessary to provide individual motors for low speeds and for high speeds and to properly switch and actuate them, and it is possible to continuously control the rotational frequency of the motor.

In the kinetofrictional force testing apparatus of this invention, a load cell sensor is made as small as possible, and the rigidity of a leaf spring is enhanced, whereby the load cell sensor including a magnetic head has its resonant frequency heightened and is appropriately damped. Furthermore, a wide range from low speed rotations to high speed rotations is covered by only one motor, thereby making it possible to continuously measure kinetic frictional force during abrupt acceleration of the magnetic disk. Moreover, since the resonant frequency of the load cell sensor is 500 Hz or above, the kinetofrictional force which occurs before the magnetic head rises above a magnetic disk having reached a rotational speed in the vicinity of 500 RPM can be precisely measured without any influence ascribable to the resonance of a system including the load cell sensor. In addition, both upwards and downwards motion of a head can be measured with a single load cell.

BRIEF DESCRIPTION OF THE DRAWING

FIG. 1 is a partly sectional side view of an embodiment of a kinetofrictional force testing apparatus according to this invention;

FIGS. 2A and 2B are respectively a side view and a plan view of the load cell of the embodiment of FIG. 1;

FIG. 3 is a block diagram of a control circuit for the embodiment of FIG. 1;

DESCRIPTION OF THE PREFERRED EMBODIMENTS

Figure 4:
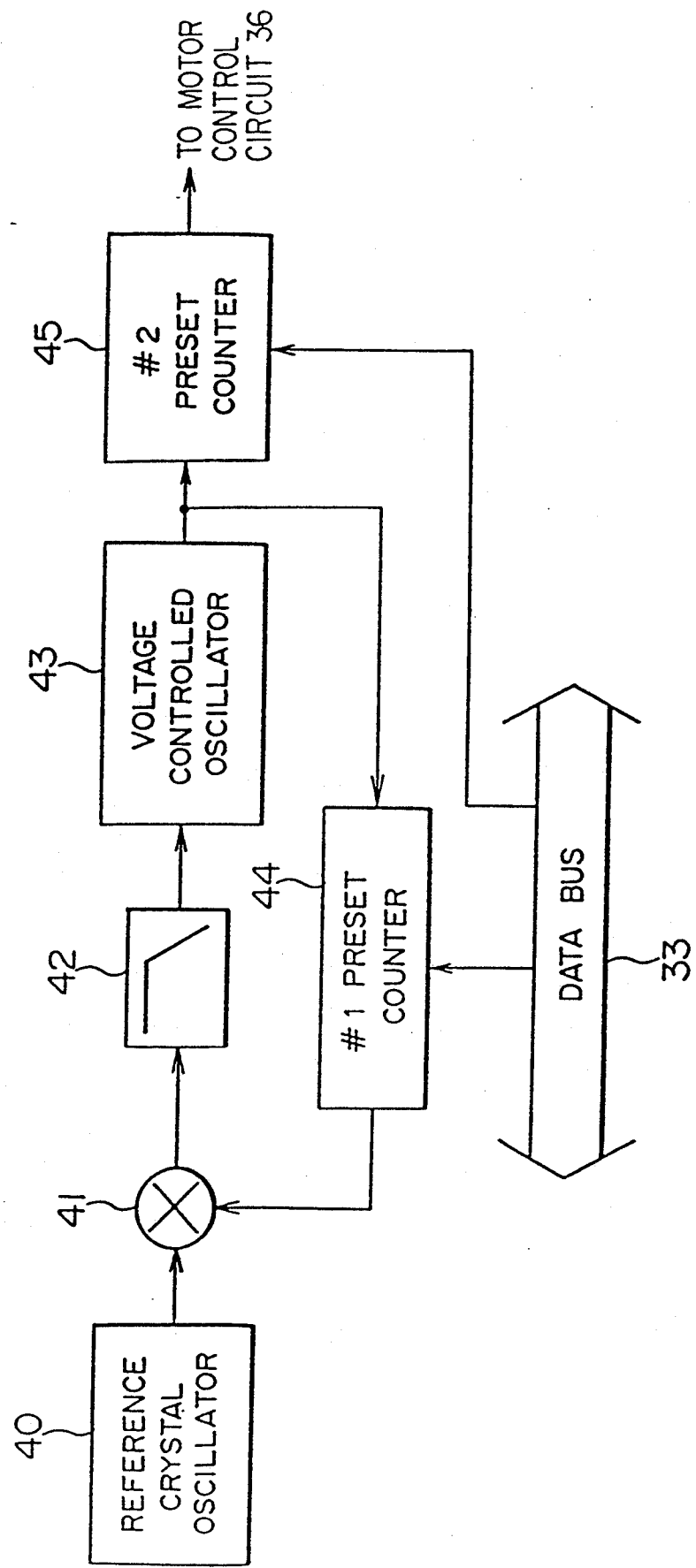
FIG. 4 is a block diagram of a rotation controlling synthesizer for the embodiment of FIG. 1.

An embodiment of a kinetofrictional force testing apparatus according to this invention will be described with reference to FIGS. 1 thru 8.

FIG. 1 is a partly cross-sectional elevation of this embodiment. In FIG. 1, numeral 1 designates a sliding member such as a magnetic disk serving as a storage medium. Numeral 2 designates a magnetic head which serves as a test head and which is made of a material based on, for example, Mn-Zn ferrite. Kinetofrictional force in the direction of rotation of the disk 1 during contact of the test head 2 with the disk is transmitted to an arm and is detected by a load cell 3. A spindle 4 and ball bearings 5 are the principal components of a mechanism for rotating the disk 1. In order to enhance the measurement accuracy of the kinetofrictional force, the rotating mechanism suppresses the vertical movements and radial movements of the disk 1 during the rotation thereof to 1 m or less and also suppresses the rotational jitters of the disk 1 to 0.1% or less. A rotating drive force for the spindle 4 is generated by a spindle motor in the form of a D.C. brushless servomotor 6 and is transmitted to the spindle 4 through a belt 7. An X-axial stage 8 and a micrometer 9 constitute a positioning mechanism for positioning the magnetic head 2.

FIGS. 2A and 2B are a side view and a plan view, respectively of the load cell of the embodiment of FIG. 1. The kinetofrictional force between a magnetic head 20 and a magnetic disk 1 (not shown) as received by the former is transmitted to magnetic head gimbals 21 connected to the magnetic head 20. A leaf spring 23 made of stainless steel and having adequately adjusted properties is vibrated according to the kinetofrictional force through a magnetic head gimbals fixture 22 to which the magnetic head gimbals 21 are attached. The leaf spring 23 has first and second lateral surfaces that extend substantially transversly, i.e., perpendicularly with respect to the plane of a magnetic disk 1 mounted on the spindle 4. The kinetofrictional force in terms of the vibrations is detected by strain gauge sensors 24 which are attached to both lateral surfaces of the leaf spring 23. Output signals corresponding to the detected kinetofrictional force are transmitted to suitable amplifiers (not shown) through an output cord 25. A three-point leveling mechanism 26 serves to set the spacing and parallelism between the magnetic disk 1 and the magnetic head gimbals fixture 22 with an accuracy within 0.01 mm. A leaf spring supporter 27 and a leaf spring fixture 28 hold the zero point of the leaf spring 23 stable for a long term. Set screws for a limiter 29 prevent the strain gauge sensors 24 from damage, and they limit the range of movement of the strain gauge sensors 24 lest predetermined detecting ranges should be exceeded. The various elements mentioned above are mounted on a frame 20A.

FIG. 3 is a block diagram of a control circuit for this embodiment. In general, the embodiment is controlled in such a way that instructions and commands transmitted over a data bus 33 are executed on the basis of programs which are set in a personal computer 34. In the arrangement of FIG. 3, the kinetofrictional force detected by a load cell sensor 30 is amplified by a succeeding load cell amplifier 31 and is converted into a corresponding digital value by an A/D converter 32. Thereafter, the digital value is sent through the data bus 33 and is read by the personal computer 34. The sensitivity of the load cell sensor 30 is symmetric in both the normal and reverse directions in which the kinetofrictional force acts. More specifically, a voltage which corresponds to the output from the load cell sensor 30 is positive during the rotation of the magnetic disk 1 in the counterclockwise (CCW) direction, and it is negative during the rotation thereof in the clockwise (CW) direction. The rotational direction of the magnetic disk 1 is designated by a rotational direction control switch 36A.

The rotation of a motor 37 in the form of a D.C. brushless servomotor is digitally controlled by executing a program set in the personal computer 34. The control of rotation and stopping of the motor 37 is performed by a motor control circuit 36 on the basis of a motor clock signal output from a rotational frequency controlling synthesizer 35 and a motor ON/OFF signal output from a parallel interface 39, these units 35 and 39 being operated by instructions or commands from the personal computer 34. The rotational frequency of the motor 37 is controlled under the management of the rotational frequency controlling synthesizer 35 in a loop comprising the motor control circuit 36, the motor 37, and a rotary encoder 38.

FIG. 4 is a diagram of an example of the rotational frequency controlling synthesizer 35 of the embodiment of FIG. 1. Reference pulses of frequency $F_0$ from a reference crystal oscillator 40 are input to a phase comparator 41 in which the phase of the reference pulses is compared with that of a signal obtained by dividing the frequency of an output from a voltage-controlled oscillator 43 by means of a #1 preset counter 44. A signal which corresponds to the component of the resulting phase difference is applied to the voltage control terminal of the voltage-controlled oscillator 43 through a low-pass filter 42. A closed loop comprising the phase comparator 41, low-pass filter 42, voltage-controlled oscillator 43, and #1 preset counter 44 forms a negative feedback loop, whereby the output signal of the voltage-controlled oscillator 43 oscillates with the following predetermined set value:

(reference frequency)×(frequency division ratio of
1 preset counter 44)

By employing such a so-called "PLL synthesizer system", the rotational frequency of the motor 37, which is a D.C. brushless servomotor, is determined by the frequency of motor clock pulses impressed from the motor control circuit 36. By jointly employing a #2 preset counter 45, the rotational frequency of the motor 37 can be designated with a resolution of 1 RPM for 10-4000 RPM, and a resolution of 0.1 RPM for 0.1-10 RPM.

Figure 5:
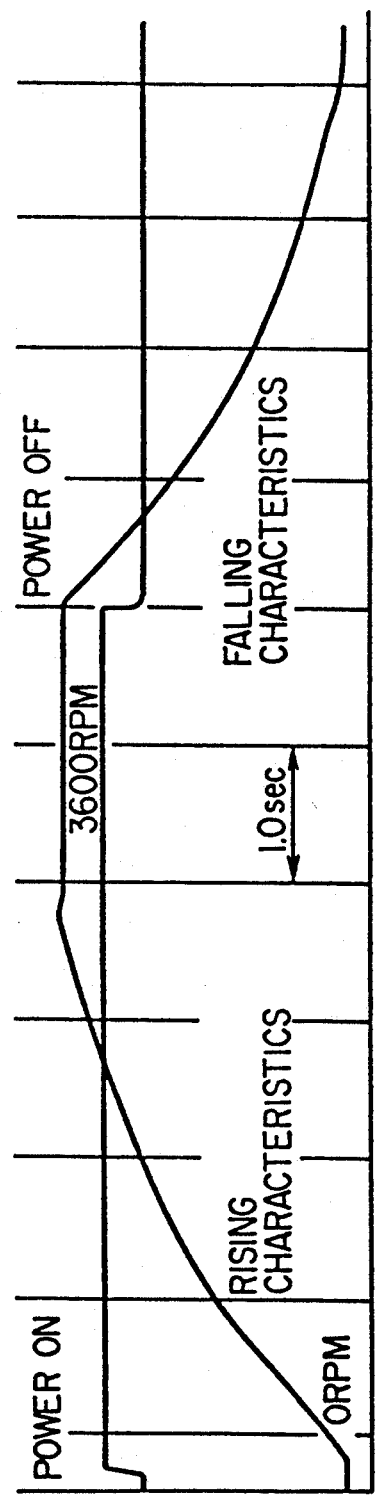
FIGS. 5 through 8 are graphs for expanding the operation of the embodiment of FIG. 1.
Figure 6:
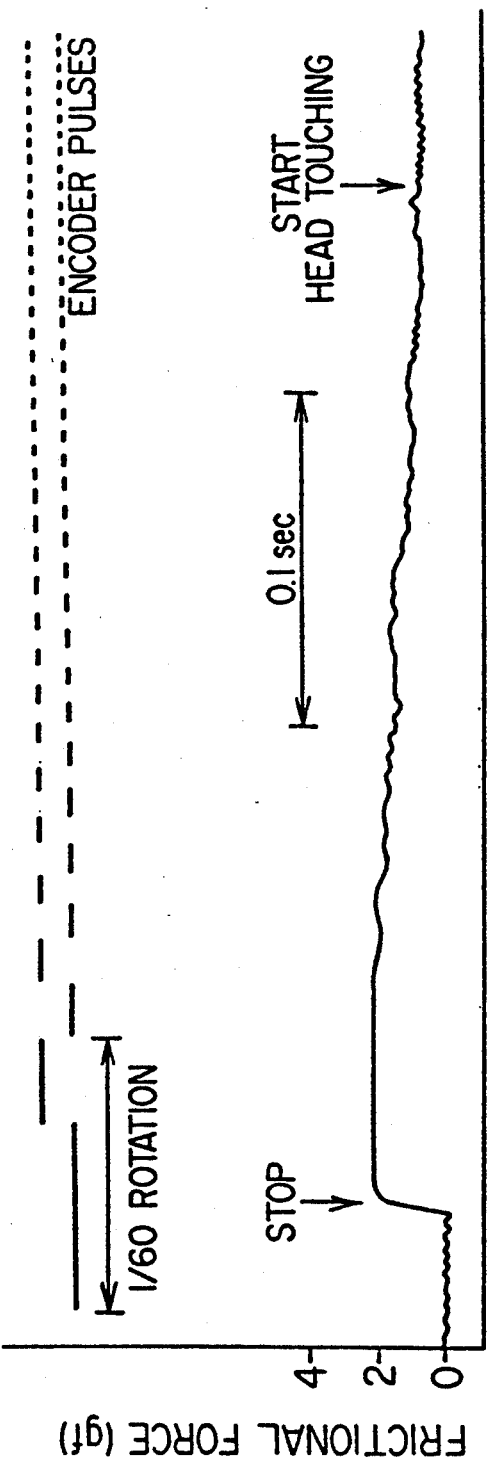
Figure 7:
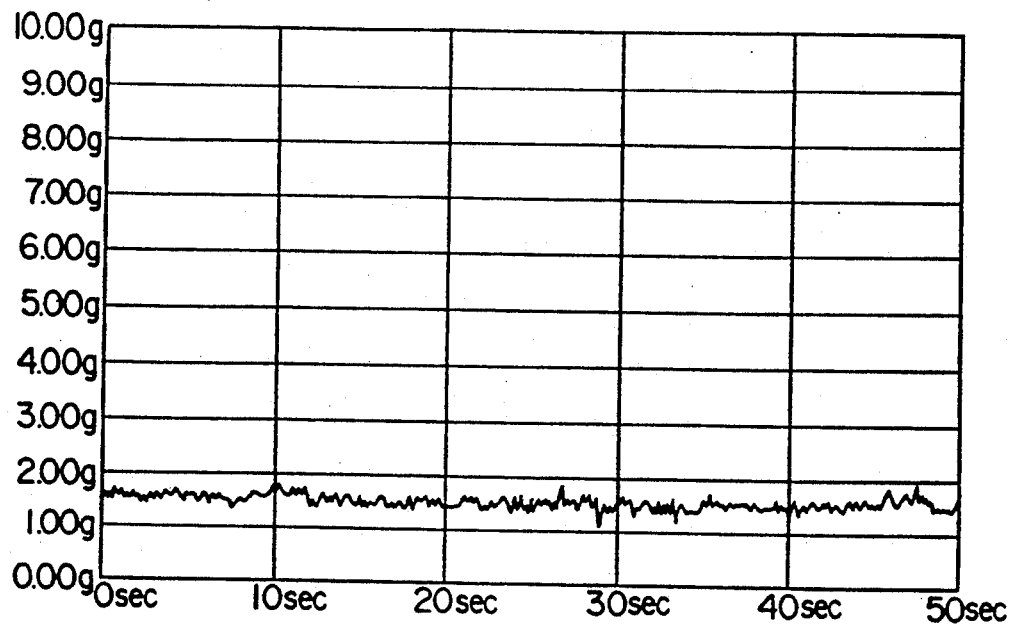
Figure 8:
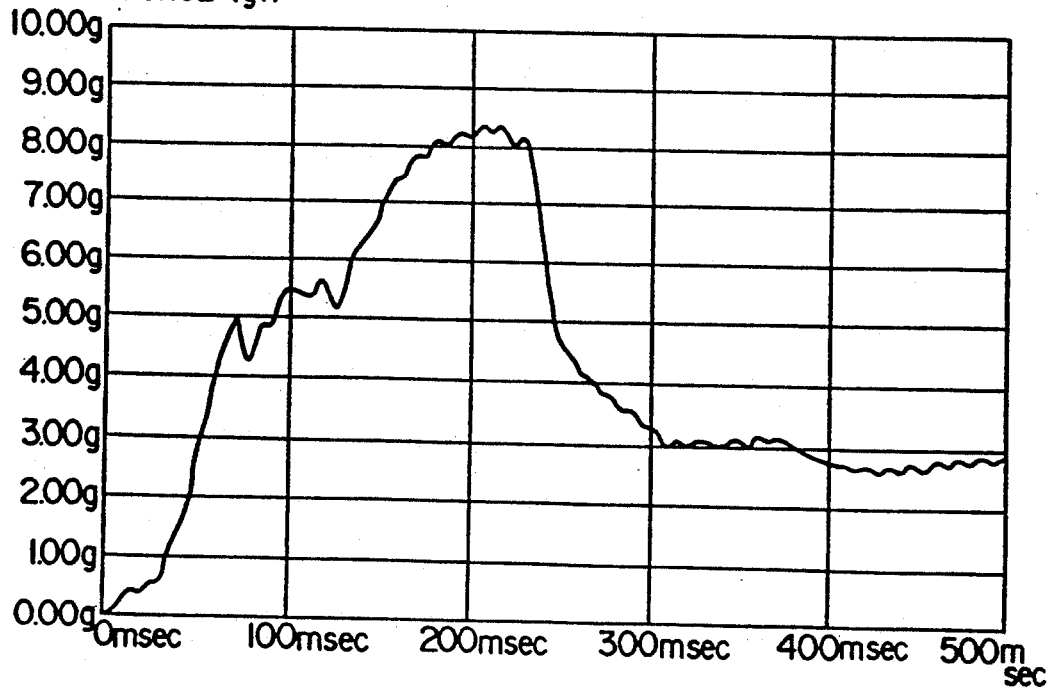

FIGS. 5 through 8 are graphs for explaining the operation of the embodiment of FIG. 1. First, FIG. 5 illustrates the characteristic curves of the rise and fall of the rotational speed of a disk in the case where the embodiment is applied to a commercially available magnetic disk device. In this figure, the abscissa is time while the ordinate is rotational frequency. FIG. 6 exemplifies measurements of the relative kinetofrictional forces between a magnetic disk and a magnetic head during the fall of rotational speed in FIG. 5. In the example of FIG. 6, 60 pulses per revolution are generated as the encoder pulses of a spindle. The magnetic head which floats above the magnetic disk at 3600 RPM begins its contact with the magnetic disk at 200 RPM and comes to a standstill after the lapse of about 0.3 seconds. The maximum frictional force on that occasion is 2 gf. FIG. 7 illustrates the frictional force of the magnetic disk, while FIG. 8 illustrates the frictional force at the attraction of the magnetic disk to the magnetic head. In each of FIGS. 7 and 8, the abscissa is time and the ordinate is frictional force.

As thus far described, in the embodiment of FIG. 1, the motor clock pulses for determining the rotational frequency of the motor are digitally controlled on the basis of the PLL system. It is therefore possible, by employing an inexpensive personal computer, to readily set the rotational frequency at intervals on the order of milliseconds and to establish the same degrees of rotational rise/fall characteristics as those of magnetic disk devices which are commercially available. As expedients for heightening the resonant frequency of the load cell sensor, the sensor system in the load cell sensor, including the magnetic head fixture, leaf spring, leaf spring fixture, etc., is reduced in size as a whole, a single leaf spring of high rigidity, the properties of which have been adjusted, is used and the mechanism for supporting the leaf spring is formed of a cantilever. In addition, high sensitivity strain gauge sensors are mounted on both lateral surfaces of the leaf spring, whereby the sensitivity of the apparatus is doubled. The magnitudes of strains responsive to the stress of the leaf spring are equalized in both the sideward directions, thereby making it possible to obtain similar measured results even when the rotating direction of the spindle is changed. Further, when zero adjustments for the kinetofrictional force are performed with the magnetic disk and the magnetic head lying in contact, ordinarily the zero point becomes unstable on account of stresses remaining in the part of the contact. In contrast, the embodiment of this invention is endowed with the function of resetting the zero points of the strain gauge sensors in programmed fashion after the magnetic head has completely risen above the magnetic disk, and it therefore holds the zero points stable for a long term.

As described above, according to this invention, it is possible to measure with a high sensitivity and with a quick response a kinetic relative frictional force which arises when a magnetic disk is rotated in contact with a magnetic head.

What is claimed is:

1. A kinetrofrictional force testing apparatus comprising:
    a variable speed motor having a rotational speed range;
    a spindle which is driven and rotated by said motor to rotate a disk in a plane of rotation at varying speeds within the range;
    a load cell fixture which supports a test head in opposition to the plane of rotation and includes sensing elements which generate electrical signals corresponding to frictional forces when the test head is in contact with a disk rotating in the plane of rotation;
    a rotational frequency controlling synthesizer and a motor control circuit connected to control speed of the motor; and
    a computer which operates the synthesizer and control circuit according to a program to vary the rotational speed of the motor to carry out a test procedure to determine relative kinetofrictional forces between the disk and the test head when in contact and when their relative speed varies at intervals according to a predetermined characteristic curve, and which receives signals form the sensing elements representing varying frictional forces between the test head and the disk, whereby the program which causes the computer to vary the rotational speed of the motor and rotational rise and fall of the disk also causes the computer to process the signals from the sensing elements and provide output data representing the measured frictional forces.

2. A kinetofrictional force testing apparatus as defined in claim 1, wherein said load cell fixture includes a stiff leaf spring which is supported by a leaf spring supporter, and test head gimbals supporting said test head on said leaf spring supporter.

3. A kinetofrictional force testing apparatus as defined in claim 2, wherein said sensing elements comprise strain gauge sensors mounted on both side surfaces of said single leaf spring.

4. A kinetofrictional force testing apparatus as defined in claim 1, wherein a zero point for a kinetofrictional force is automatically reset on the basis of the predetermined program in said computer, when said test head begins flying above a surface of said disk.

5. A kinetofrictional force testing apparatus comprising:
    a spindle for supporting a disk in a plane of rotation;
    a motor drivingly connected to the spindle for rotating the spindle;
    a leaf spring having an end and first and second lateral surfaces extending substantially perpendicular to the plane of rotation;
    a test head supported by the end of the leaf spring in a position opposing the plane of rotation; and
    first and second force sensing elements comprising first and second strain gages attached to the first and second lateral surfaces of the leaf spring for generating electrical signals corresponding to forces applied to the leaf spring due to frictional forces when the test head is in contact with a disk rotating in the plane of rotation.

6. A testing apparatus as claimed in claim 5 wherein the leaf spring has a thickness that is less than the width of the first and second surfaces of the leaf spring.

7. A testing apparatus as claimed in claim 5 wherein the motor is a variable speed motor.

8. A testing apparatus as claimed in claim 7 further comprising a programmable motor speed controller for controlling the rotational speed of the motor according to a predetermined pattern.

9. A testing apparatus as claimed in claim 5 further comprising means for zeroing the output of the force sensing elements when the test head is not in contact with a disk rotating in the plane of rotation.

10. A testing apparatus as claimed in claim 5 further comprising gimbals connected between the leaf spring and the test head, the gimbals pressing the test head towards the plane of rotation and enabling the test head to float above the surface of a disk rotating in the plane of rotation when the rotational speed exceeds a prescribed level.

* * * * *